United States Patent
Qiulin et al.

(10) Patent No.: US 10,111,638 B2
(45) Date of Patent: Oct. 30, 2018

(54) APPARATUS AND METHOD FOR REGISTRATION AND REPROJECTION-BASED MATERIAL DECOMPOSITION FOR SPECTRALLY RESOLVED COMPUTED TOMOGRAPHY

(71) Applicant: TOSHIBA MEDICAL SYSTEMS CORPORATION, Otawara-shi (JP)

(72) Inventors: Tang Qiulin, Buffalo Grove, IL (US); Yu Zhou, Wilmette, IL (US); Satoru Nakanishi, Utsunomiya Tochigi (JP); Richard Thompson, Hawthom Woods, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 22 days.

(21) Appl. No.: 15/163,404

(22) Filed: May 24, 2016

(65) Prior Publication Data
US 2017/0340304 A1 Nov. 30, 2017

(51) Int. Cl.
- G06K 9/00 (2006.01)
- A61B 6/00 (2006.01)
- A61B 6/03 (2006.01)

(52) U.S. Cl.
CPC ............ *A61B 6/5264* (2013.01); *A61B 6/032* (2013.01); *A61B 6/482* (2013.01)

(58) Field of Classification Search
None
See application file for complete search history.

(56) References Cited

U.S. PATENT DOCUMENTS

| | | |
|---|---|---|
| 6,035,012 A | 3/2000 | Hsieh |
| 6,934,357 B2 | 8/2005 | Boyd et al. |
| 7,272,429 B2 | 9/2007 | Walker et al. |
| 7,940,892 B2 | 5/2011 | Akahori |
| 8,503,750 B2 | 8/2013 | Benson et al. |
| 9,025,815 B2 | 5/2015 | Wu et al. |
| 2006/0067473 A1* | 3/2006 | Eberhard ............... A61B 6/025 378/98.9 |

* cited by examiner

*Primary Examiner* — Atiba O Fitzpatrick
(74) *Attorney, Agent, or Firm* — Oblon, McClelland, Maier & Neustadt, L.L.P.

(57) ABSTRACT

A method and apparatus is provided to perform material decomposition based on spectral computed tomography (CT) projection data generated using registered reconstructed images. Registration is performed in the image domain, whereas material decomposition is performed in the sinogram domain. In the sinogram domain, material decomposition can include beam-hardening corrections. For at least two energy components, CT images are reconstructed, and registration is performed among the CT images. In certain implementations, the registered images are forward projected, and material decomposition is based on the resultant forward projections. In other implementations, motion images are generated from differences between the reconstructed CT images pre- and post-registration. The projection data is then corrected using forward projections of the motion images, and material decomposition is performed using the motion-corrected projection data.

20 Claims, 5 Drawing Sheets

APPARATUS AND METHOD FOR REGISTRATION AND REPROJECTION-BASED MATERIAL DECOMPOSITION FOR SPECTRALLY RESOLVED COMPUTED TOMOGRAPHY

FIELD

This disclosure relates to decomposing spectral computed tomography (CT) projection data into material components, and more particularly to a registration process performed between CT images corresponding to different X-ray energies, wherein the registration process is performed prior to material decomposition.

BACKGROUND

Computed tomography (CT) systems and methods are widely used, particularly for medical imaging and diagnosis. CT systems generally create projection images through a subject's body at a series of projection angles. A radiation source, such as an X-ray tube, irradiates the body from one side. Images of the subject's body can be reconstructed from the projection data (i.e., the projection images acquired at various projection angles), using various reconstruction techniques such as filtered back-projection, iterative reconstruction, etc.

Many clinical applications can benefit from spectral CT technology, which can provide improvement in material differentiation and beam-hardening correction. Spectral CT data can be obtained using one of several technologies, including: direct X-ray detection using semiconductor-based photon-counting detectors, dual-source systems to perform dual-energy scans, kVp-switching systems to perform dual-energy scans, performing sequential scans at different X-ray energies, and using layered detectors capable of simultaneously measuring multiple energies to simultaneously realize a dual-energy scan. When a spectral CT system uses energy scans performed at different times, motion of the patient in between scans can introduce errors and artifacts into the material decomposition.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
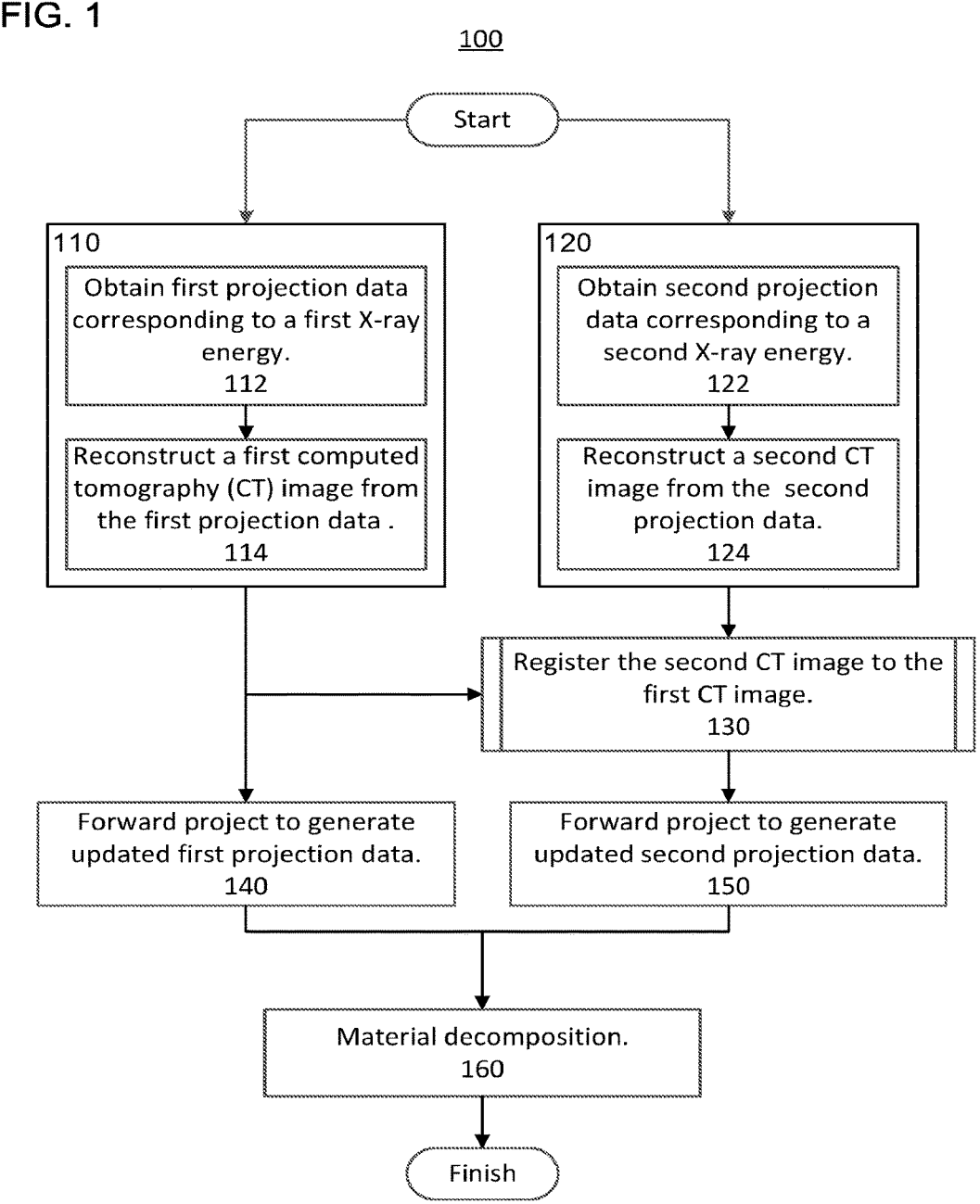
FIG. 1 shows a flow diagram of an implementation of a method of performing a material decomposition of projection data based on reprojections of registered images.

In spectral CT, radiation having multiple energy components is used to make projective measurements of an object OBJ to generate spectrally resolved projection data. These projective measurements are made at a series of projection angles, and images of the object OBJ can be reconstructed for each energy component using CT image reconstruction methods. However, unlike non-spectral CT, spectral CT generates additional information due to different materials exhibiting different X-ray attenuation as a function of the X-ray energy. These differences enable a decomposition of the spectrally resolved projection data into material components, usually two material components because there are two dominant attenuation mechanisms (i.e., Compton scattering and photoelectric absorption,) that contribute to spectral variations in the X-ray attenuation. In clinically applications, for example, the two material components of the material decomposition can be bone and muscle/water. Mapping the projection data from spectral components to the material components (i.e., the material decomposition) can be performed either before or after the image reconstruction process. However, performing material decomposition prior to the reconstruction process is preferable, due to beam-hardening considerations.

When most of the X-rays have energies well above the K-edge of the majority atoms of the imaged object OBJ, as is the case for conventional X-ray sources imaging biological objects, the material decomposition problem can be solved using only two energy components consistent with the existence of the two dominant interaction processes discussed above. Thus, spectral CT is sometimes referred to as dual-energy CT, and the material decomposition process can be referred to as dual-energy analysis. Herein, spectral CT will include at least dual-energy CT, but also includes projective measurements with more than two energy components.

A dual-energy analysis method can be used because the attenuation of X-rays in biological materials is dominated by two physical processes (i.e., photoelectric absorption and Compton scattering). Thus, the attenuation coefficient as a function of energy can be approximated by the decomposition $$\mu(E,x,y) = \mu_{PE}(E,x,y) + \mu_C(E,x,y),$$

wherein $\mu_{PE}(E,x,y)$ is the photoelectric attenuation and $\mu_C(E,x,y)$ is the Compton attenuation. Alternatively, this attenuation coefficient can be rearranged into a decomposition of a high-Z material (i.e., material 1, which can be bone) and a low-Z material (i.e., material 2, which can be water) to become $$\mu(E,x,y) \approx \mu_1(E)c_1(x,y) + \mu_2(E)c_2(x,y),$$

wherein $c_1(x, y)$ and $c_2(x, y)$ are, respectively, the first and second basis images.

When a spectral CT system uses energy scans performed at different times, motion of the patient in between scans can introduce errors and artifacts into the material decomposition. Motion between scans can be corrected using a registration process to align scans taken at different times by translating and/or rotating an image reconstructed from a second scan to agree with an image reconstructed from a first scan. Material decomposition can then be performed on the registered images. However, material decomposition in the sinogram domain prior to image reconstruction is preferable to material decomposition in the image domain after image reconstruction, due to beam-hardening considerations. Accordingly, the methods described herein provide material decomposition in the sinogram domain (i.e., using projection data rather than reconstructed images) using projection data that has been corrected using a registration process.

Thus, the methods described herein realize both the benefits of registration and the benefits of material decomposition in the sinogram domain.

One challenge of registration for projection-based material decomposition is to perform the registration process to correct the projection data for motion without introducing non-physical effects into the projection data. Without registration, motion will be interpreted by the decomposition algorithm as a material composition effect, thereby degrading the image quality of the reconstructed images. However, if the registration process introduces artifacts into registered projection data (e.g., by not handling beam hardening properly), then images based on the registered projection data will also be degraded. By performing registration while accounting for and maintaining the physical characteristics of the projection data (e.g., beam hardening), the reconstructed images will not be degraded.

In one embodiment, motion-compensated reprojection-based material-decomposition method is described herein. This method also maintains unchanged the physical characteristics of the raw data (e.g., beam hardening). Among these aspects of the raw data, beam hardening can be significant for dual-energy material decomposition. By maintaining the beam hardening effects unchanged, a more accurate reprojection-based material decomposition can be achieved.

Referring now to the drawings, wherein like reference numerals designate identical or corresponding parts throughout the several views, FIG. 1 shows a flow diagram of a method 100 for obtaining registered projection data of two scans. The two scans are taken at different energies in order to perform material decomposition, and motion between the respective scans is compensated for by the registration process, which is performed in the image domain, but material decomposition is performed in the sinogram domain. In process 110 of method 100, first projection data corresponding to a first scan at a first X-ray energy is obtained in step 112. Then in step 114 of process 110, a first image is reconstructed from the first projection data. The image reconstruction process can be performed using any of a filtered back-projection method, iterative image reconstruction methods (e.g., using a total variation minimization regularization term), a Fourier-based reconstruction method, or stochastic image reconstruction methods.

In process 120 of method 100, second projection data and a second reconstructed image are obtained at steps 122 and 124, respectively. The second projection data and the second reconstructed image correspond to a second X-ray energy and a second scan time. The second projection data and the second reconstructed image are generated in a similar manner to the first projection data and the first reconstructed image generated in process 110.

In process 130 of method 100, registration is performed between the first and second reconstructed images. Due to possible motion of a patient between the first scan and the second scan (e.g., the beating of the patient's heart for cardiac CT or fidgeting by the patient) the first and second CT images can be offset with respect to each other. Registration between the first and second reconstructed images can be used to align the two CT images and thus improve material decomposition between the images.

In step 140 of method 100, the first reconstructed image is forward projected to generate updated first projection data.

In step 150 of method 100, the second reconstructed image is forward projected to generate updated second projection data that is registered with the updated first projection data. Because the first and second updated projection data are generated using the same process, except for registration, any filtering or corrections performed by the process of back projecting and then forward projecting will be matched between the first and second updated projection data. Thus, the generation of the first and second updated projection data treats the first and second (updated) projection data symmetrically and avoids artifacts in the material decomposition due to asymmetries.

In step 160 of method 100, material decomposition is performed on the first and second updated projection data. For example, material decomposition can be performed using a cost-function method or a split-step method. In the split-step method, the material-decomposition problem is subdivided into two sub-problems, each corresponding to one half of the split-step method: (1) the detector-correction problem, and (2) the X-ray-absorption problem. Both of these sub-problems can be framed in terms of the projection lengths $L_1$ and $L_2$ of the material decomposition. The split-step method solves the material decomposition by iterating between the two sub-problems (i.e., steps). At each transition between sub-problem steps, the next sub-problem (step) uses the results from the preceding sub-problem (step) as an input. Thus, by alternating between each sub-problem (step), the split-step method repeatedly solves each sub-problem multiple times until the solutions converge to a stable value for the projection lengths $L_1$ and $L_2$.

The detector-correction sub-problem of the split-step method corresponds to the detection process of an X-ray measurement, and the X-ray-absorption sub-problem corresponds to the propagation/absorption process of the X-ray measurement. The projection lengths $L_1$ and $L_2$ are given by a line integral over the coefficients $c_1(x, y)$ and $C_2(x, y)$ along the X-ray trajectory l, which can be expressed as $$L_i = \int \int_l dx\, dy\, c_i(x, y).$$

The X-ray-absorption problem represents the change in the X-ray intensity as the X-ray is attenuated by propagating from the X-ray source and through an object OBJ until the X-ray arrives at an X-ray detector. The incident X-ray flux S(E) onto each detector is given by $$S(E) = n_{air} S_0(E) \exp[-\mu_1(E)L_1 - \mu_2(E)L_2],$$

wherein $n_{air}$ is the X-ray flux from the X-ray source onto the object OBJ that is being imaged, $L_1$ and $L_2$ are projection lengths given by the line integrals along the X-ray trajectory and correspond respectively to the first and second material of the material decomposition, and $S_0(E)$ is a normalized spectrum of the incident X-ray flux as a function of energy E (e.g., $\int dE\, S_0(E) = 1$).

Second, the detector-correction problem corresponds to a mapping from the incident
X-ray flux on the X-ray detectors to the measured counts by the X-ray detectors. The mapping from the incident flux on the X-ray detectors to the measured counts can be nonlinear and can depend on the incident flux S(E) on the X-ray detectors. Thus, the detector-correction problem depends on the projection lengths $L_1$ and $L_2$ because the detector-correction problem depends on the incident flux S(E).

On the one hand, the detector-correction problem uses the incident flux S(E), which includes the information of the projection lengths $L_1$ and $L_2$, to calculate corrected projection data. On the other hand, the X-ray-absorption problem uses the corrected projection data from the detector-correction problem to calculate the projection lengths $L_1$ and $L_2$, which are in turn used to calculate the incident flux $S(E)$. Thus, each sub-problem incorporates as an input the output generated by the previous sub-problem.

The split-step method is performed by alternating between using the projection lengths $L_1$ and $L_2$ to update the corrected projection data and then using the updated corrected projection data to update the projection lengths $L_1$ and $L_2$, which then are used to update the corrected projection data, and so forth until convergence. After iterating between these two steps multiple times, the projection lengths $L_1$ and $L_2$ converge and the result is output as the material decomposition. Details of certain implementations of the split-step method are provided in U.S. patent application Ser. No. 14/593,818, incorporated herein by reference in its entirety, wherein the split-step method is referred to as the iterative method.

An alternative to the split-step method is the cost-function method, which also performs the material decomposition. In the cost-function method, a pair of projections lengths $L_1$ and $L_2$ is used to calculate model projection data, and the model projection data is compared to the actual projection data using a cost function. Smaller values of the cost function correspond to closer agreement between the actual projection data and the model projection data. Convex optimization can be used to find the pair of projections lengths $L_1$ and $L_2$ that minimize the cost function, and this pair of projection lengths are the material decomposition. The model projection data is calculated using a model that includes both the absorption arising from transmission through the object OBJ and a detector-response model of the X-ray detectors. Thus, the two sub-problems of the split-step method are simultaneously solved by minimizing the cost-function method. Details of the cost-function method are provided in U.S. patent application Ser. No. 14/603,135, incorporated herein by reference in its entirety. Further, U.S. patent application Ser. No. 14/674,594, incorporated herein by reference in its entirety, provides additional details regarding the detector-response model used in the material decomposition methods described herein.

Figure 2:
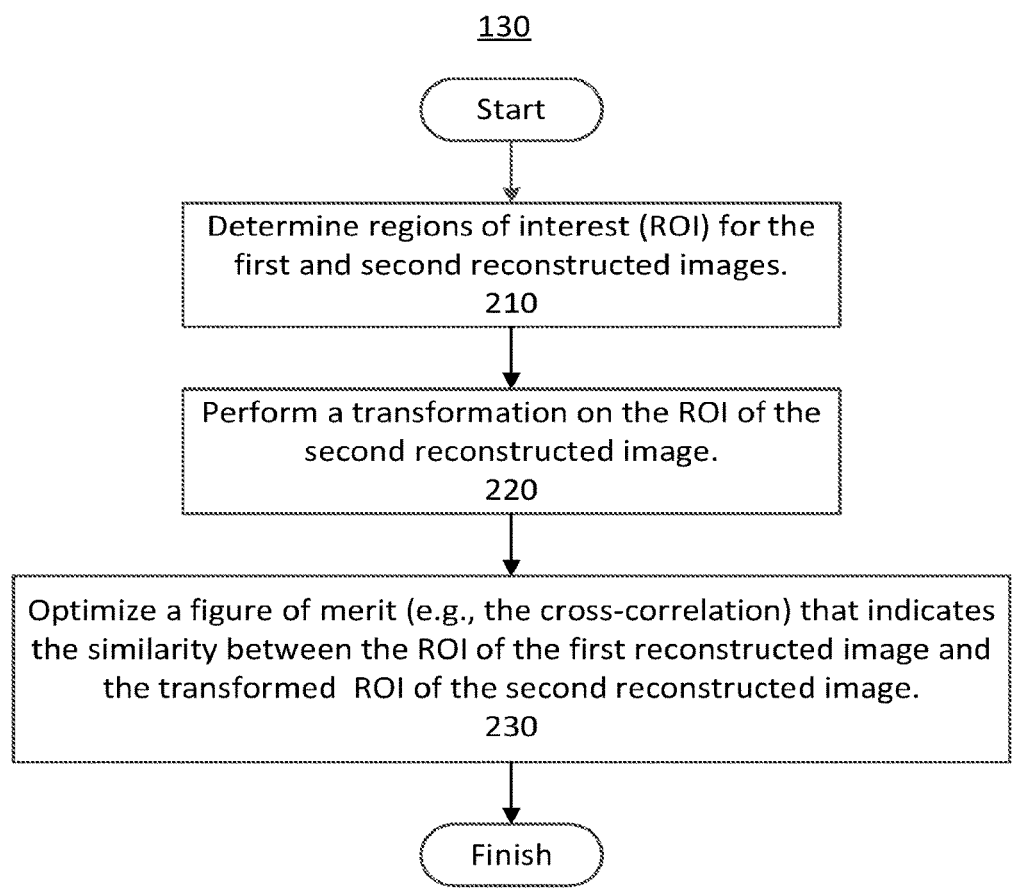
FIG. 2 show a flow diagram of an implementation of a process of registering a second image to a first image.

FIG. 2 show a flow diagram of process 130. Registration can be performed by finding the maximum value of the cross-correlation function between the first reconstructed image and the second reconstructed image, wherein the cross-correlation function can include both translations and rotations. Alternatively, registration can be performed by solving for the argument (i.e., transformation) that maximizes an overlap integral between the first reconstructed image and the second reconstructed image, wherein the argument of the transformation operator includes both translations and rotations.

The first reconstructed image $P_n(u,v)$ and the corresponding second reconstructed image $P_{n+1}(u,v)$ are described using spatial coordinates u and v, which can be the spatial indices of a grid of the reconstructed images (e.g., a uniform grid $u=u^{(0)}+j\Delta u$ and $v=v^{(0)}+k\Delta v$, wherein $\Delta u$ and $\Delta v$ are the spatial separations between pixels). Here, two-dimensional, rather than three-dimensional, reconstructed images are considered to simplify the notation, but the generalization to three-dimensional reconstructed images is straightforward. Further, without loss of generality, only registration of two images is described, but the same process can be used for additional reconstructed images.

In step 210 of process 130, a region of interest (ROI) is determined for the first reconstructed image, and a similar ROI is determined for the second reconstructed image. The ROI of the first reconstructed image can be described with reference to the top-left pixel $P_n(u_0, v_0)$ and the right-bottom pixel $P_n(u_1, v_1)$. Thus, the first reconstructed image in the ROI ("ROI of the first reconstructed image") can be expressed as $$P_{n+1,roi}(u',v')=P_{n+1}(u_0+u',v_0+v'), 0\le u'\le u_1-u_0, 0\le v'\le v_1-v_0.$$

Similarly, the corresponding second reconstructed image in ROI ("ROI of the second reconstructed image") can be expressed as $$P_{n+1,roi}(u', v')=P_{n+1}(u_0+u', v_0+v'), 0\le u'\le u_1-u_0, 0\le v'\le v_1-v_0.$$

In step 220 of process 130, the ROI of second reconstructed image is transformed. The ROI of the second reconstructed image can be transformed by the transformation operator T, and the pixel values within the ROI of the transformed second reconstructed image can be interpolated and mapped onto a grid matching the first reconstructed image in order to calculate the overlap integral. A rigid transformation (defined as rotation and translation) of the ROI in the second reconstructed image can be defined as $$(u_{0,T},v_{0,T})=T(j_0,v_0)=R_\theta(u_0,v_0)+(\Delta u, \Delta v) \text{ and}$$

$$(u_{1,T},v_{1,T})=T(u_1,v_1)=R_\theta(u_1,v_1)+(\Delta u, \Delta v); \text{ and}$$

the second reconstructed image in the transformed ROI can be expressed as $$P_{C,roi}(u',v',T)=P_C((u_{0,T}, v_{0,T})+u\vec{u}+v\vec{u}, 0\le u'\le u_1-u_0, 0\le v'\le v_1-v_0,$$

wherein $\vec{u}$ and $\vec{u}$ are normalized vectors along transformed u and v directions. The transformation of the ROI image in a second reconstructed image can be implemented by image interpolation to map the second snap shot onto a grid with a matching size ($u_1-u_0$, $v_1-v_0$) with the ROI of the first reconstructed image.

In step 230 of process 130, a figure of merit is calculated as a function of the transformation operator T, and the argument T optimizing the figure of merit is output. Here the process 130 is exemplified using a cross-correlation as the figure of merit. The cross-correlation between the ROI of the first reconstructed image and the transformed ROI of second reconstructed image can be expressed by $$CC(T)=\sum_{u'=0}^{u_1-u_0}\sum_{v'=0}^{v_1-v_0}\frac{(P_{n,roi}(u',v')-\overline{P}_{n,roi})(P_{n+1,roi}(u',v',T)-\overline{P}_{n+1,roi})}{(u_1-u_0)(v_1-v_0)},$$

wherein $\overline{P}_{n,roi}$ and $\overline{P}_{n+1,roi}$ are the average in ROI of the first reconstructed image $P_{n,roi}$ (u', v') and the average in ROI of transformed second reconstructed image $P_{n+1,roi}$(u', v', T), respectively. Registration occurs by finding the transformation that maximizes the above cross-correlation. For example, an optimal transformation maximizing the cross-correlation between the ROIs of the first and second reconstructed images can be obtained using a brute force search within a pre-defined searching region so that a transformation argument is obtained that maximizes the cross-correlation as expressed by $$\tilde{T}=\underset{T}{\text{argmax}}\{CC(T)\}$$

The registered second reconstructed image then becomes $$P_{n+1,reg}(u,v) = P_{n+1}(\tilde{T}(u,v)).$$

The registered second reconstructed image can be obtained by interpolation of the second reconstructed image and mapping onto a grid corresponding to the transformed ROI. In one implementation, a stochastic search method, such as a genetic algorithm, can be used rather than a brute force search. In one implementation, a gradient search method can be used rather than the brute force search. Any known search method can be used to optimize the transformation argument of the cross-correlation function.

Figure 3:
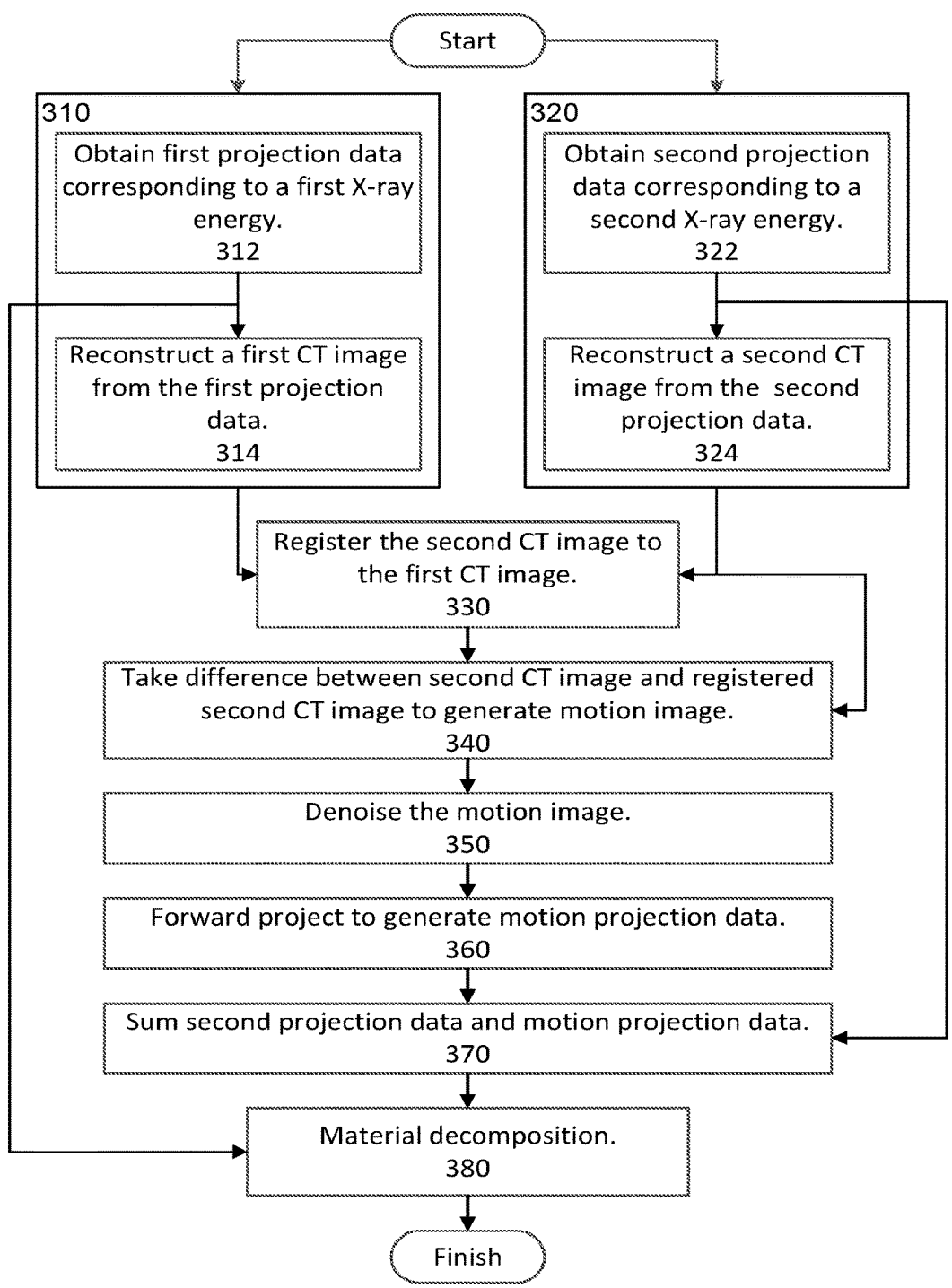
FIG. 3 shows a flow diagram of an implementation of a method of performing a material decomposition using motion-corrected projection data.

FIG. 3 shows a flow diagram of a method 300 of obtaining registered projection data of two energy scans.

In process 310 of method 300, first projection data corresponding to a first scan at a first X-ray energy is obtained in step 312. Then in step 314 for process 310 a first image is reconstructed from the first projection data. The image reconstruction process can be performed using a filtered back projection method, iterative image reconstruction methods (e.g., using a total variation minimization regularization term), a Fourier-based reconstruction method, or stochastic image reconstruction methods.

In process 320 of method 300, second projection data and a second reconstructed image are obtained at steps 322 and 324 respectively. The second projection data and the second reconstructed image correspond to a second X-ray energy and a second scan time. These are generated in a similar manner to the first projection data and the first reconstructed image generated in process 310.

In process 330 of method 300, registration is performed between the first and second reconstructed images. Process 330 can be performed similarly to process 130.

In step 340 of method 300, a motion image is generated by taking a difference between the second reconstructed image without registration and the second reconstructed image with registration.

In step 350 of method 300, denoising is performed on the motion image. In certain implementations, step 350 can be omitted. Various denoising methods can be applied to the motion images, including: linear smoothing filters, anisotropic diffusion, non-local means, and nonlinear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors; the Gaussian Filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume the homogeneity could be found in the local neighbourhood are homogeneous and therefore tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were a spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In addition a filter using a total-variation (TV) minimization regularization term can be used where it is assumed that the areas being imaged are uniform over discrete areas with relatively sharp boundaries between the areas. A TV filter can also be used as another example of a nonlinear filter.

In non-local means filtering, rather than performing a weighted average of pixels according to their spatial proximity, pixels are determined to be a weighted average according to the similarity between patches within the images. Thus, noise is removed based on non-local averaging of all the pixels in an image—not just the neighboring pixels. In particular, the amount of weighting for a pixel is based on the degree of similarity between a small patch centered near that pixel and another small patch centered around the pixel being denoised.

Figure 4:
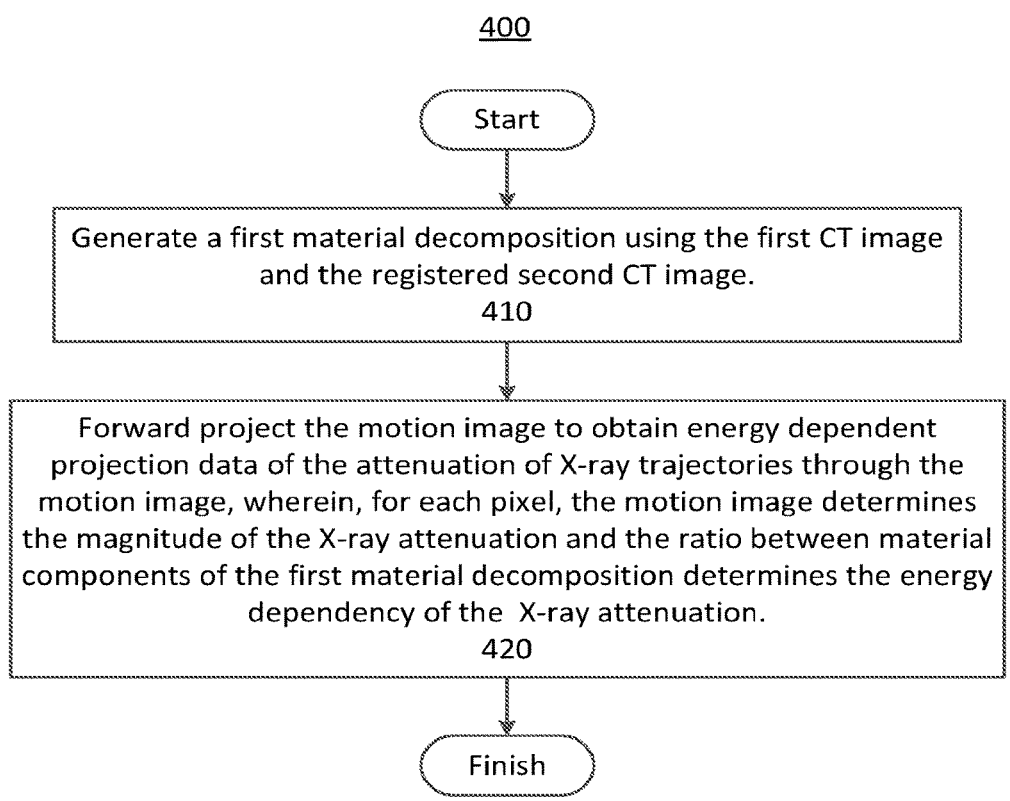
FIG. 4 shows a flow diagram of an implementation of a method of forward projecting to account for energy dependent X-ray attenuation of various material components.

In step 360 of method 300, motion projection data is generated by performing forward projection of the X-ray attenuation along the X-ray trajectories through the motion image and incident on the respective detector elements. If the reconstructed images are corrected for beam hardening, then the forward projection will account for variations of the X-ray attenuation as a function of the X-ray energy. FIG. 4 shows a flow diagram of a method 400 to account for variations in the X-ray attenuation as a function of X-ray energy during forward projections.

In step 370 of method 300, the second projection data is corrected for motion by combining the second projection data with the corresponding motion projection data. For example, the second projection data and the motion projection data can be combined using either subtraction or addition depending on whether the motion projection image is the second CT image minus the registered second CT image or vice versa.

In step 380 of method 300, material decomposition is performed using the first projection data and the corrected second projection data. For example, material decomposition can be performed using any of the methods discussed for step 160 of method 100.

FIG. 4 shows a flow diagram of the method 400. Method 400 accounts for variations as a function of X-ray energy in the X-ray attenuation during forward projections.

In step 410 of method 400, a first material decomposition is performed using the first CT image and the registered second CT image. The first material decomposition generates a first material-component image and a second material-component image.

In step 420 of method 400, the motion image is forward projected to generate motion projection data that is a function of the X-ray energy. For each pixel (herein the word "pixel" can mean any type of pixel, including, for example, a two-dimensional pixel or a three-dimensional volume pixel or voxel) in the motion image, the dependence of the attenuation on the X-ray energy can be determined as a linear superposition of the energy dependent attenuation coefficients of the material components of the material decomposition, wherein the weights of the linear superposition are determined from the ratio between the respective pixel values of the first and second material-component images corresponding to the same pixel location as the pixel of the motion image. The motion projection data is then obtained by integrating the energy dependent attenuation over the X-ray spectrum of the second projection data. Thus, beam-hardening effects can be incorporated into the forward projection of the motion image.

The inclusion of beam-hardening effects into the forward projection is important when the X-ray source does not closely approximate a mono-energetic source, and when the image reconstruction of the first and second CT images includes beam-hardening corrections. If, on the other hand, the image reconstruction of the first and second CT images does not include beam-hardening corrections, then a forward projection without energy dependent attenuation coefficients is used.

In addition to beam-hardening corrections, the CT image reconstruction can include scatter corrections and various other corrections and calibrations to correct for known distortions and artifacts of the X-ray measurements.

Additionally, the above methods can be performed with projection data for more than two energy components. Each additional energy component can be used to reconstruct a CT image, which is then registered to the first CT image. Further, material decomposition can be performed using a forward projection of the registered CT images and the first CT image, as described in method 100. Alternatively, material decomposition can be performed using the first CT image and corrected CT images obtained using motion images, as described in method 300.

Figure 5:
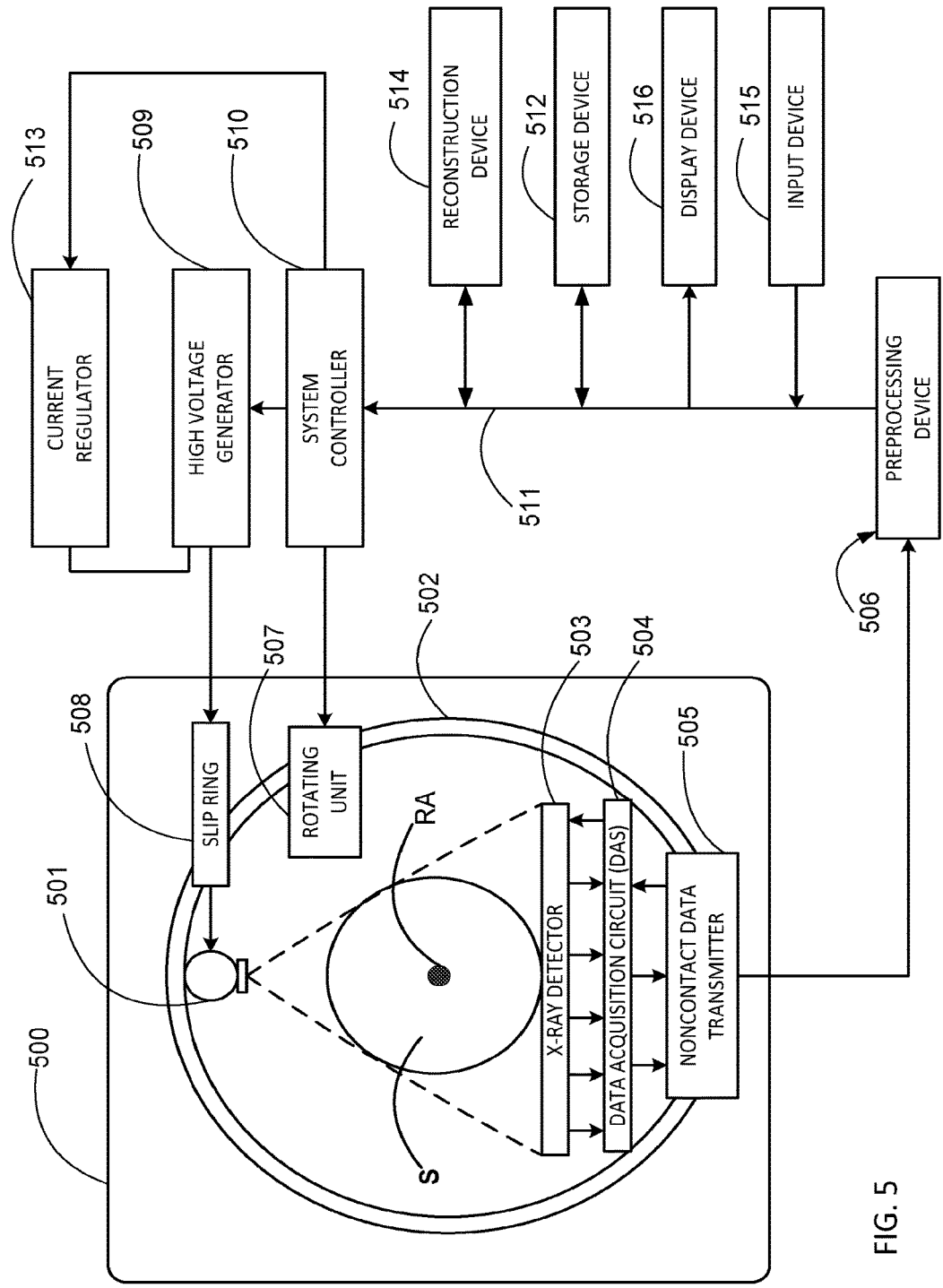
FIG. 5 shows a schematic diagram of an implementation of an X-ray CT apparatus configured to acquire projection data.

FIG. 5 illustrates an implementation of the radiography gantry included in a CT apparatus or scanner. As shown in FIG. 5, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing the CT image reconstruction, registration, reprojection, motion correction, and material decomposition methods include in methods 100, 300, and 400 discussed herein.

The reconstruction device 514 can execute the methods 100, 300, and 400 discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can be performed using filtered back projection, iterative image reconstruction methods, or stochastic image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
processing circuitry configured to
obtain first projection data representing an intensity of first radiation incident at a plurality of detector elements, the first radiation having a first photon energy;
obtain second projection data representing an intensity of second radiation incident at the plurality of detector elements, the second radiation having a second photon energy;
register a reconstructed image of the second projection data to a reconstructed image of the first projection data;
update the second projection data using the registered reconstructed image of the second projection data; and
perform material decomposition using the updated second projection data and an updated first projection data or the first projection data.

2. The apparatus of claim 1, wherein the processing circuitry is further configured to
forward project the registered reconstructed image of the second projection data to generate processed second projection data as the updated second projection data,
forward project the reconstructed image of the first projection data to generate processed first projection data, and
perform material decomposition using the processed first projection data and the processed second projection data.

3. The apparatus of claim 1, wherein the processing circuitry is further configured to
generate a motion image by taking a difference between the reconstructed image of the second projection data without registration and the registered reconstructed image of the second projection data,
forward project the motion image to generate motion projection data,
combine the motion projection data with the second projection data to generate corrected second projection data as the updated second projection data, and
perform material decomposition using the first projection data and the corrected second projection data.

4. The apparatus of claim 3, wherein the processing circuitry is further configured to denoise the motion image before the forward projection of the motion image to generate motion projection data.

5. The apparatus of claim 3, wherein the processing circuitry is further configured to perform the forward projection of the motion image by determining attenuation of the second radiation as a function of photon energy of the second radiation.

6. The apparatus of claim 3, wherein the processing circuitry is further configured to register the reconstructed image of the second projection data to the reconstructed image of the first projection data by
maximizing a cross-correlation between the reconstructed image of the first projection data and a transformation of the reconstructed image of the second projection data, wherein
the transformation includes a translation.

7. The apparatus of claim 3, wherein the processing circuitry is further configured to register the reconstructed image of the second projection data to the reconstructed image of the first projection data by
optimizing a similarity measure between the reconstructed image of the first projection data and a transformation of the reconstructed image of the second projection data, wherein
the transformation includes a rotation.

8. The apparatus of claim 3, wherein the processing circuitry is further configured to denoise the motion image using an edge-preserving filtering method.

9. The apparatus of claim 5, wherein the processing circuitry is further configured to perform the forward projection of the motion image by
materially decomposing the registered reconstructed image of the second projection data and the reconstructed image of the first projection data to generate a first material decomposition, and
determining the attenuation of the second radiation as a function of the photon energy using the first material decomposition and using attenuation coefficients as a function of the photon energy of material components of the first material decomposition.

10. The apparatus of claim 1, wherein the processing circuitry is further configured to
obtain a plurality of projection data representing radiation intensities incident on the plurality of detectors, the radiation intensities corresponding to a plurality of photon energies, and the plurality of projection data including the second projection data, but not including the first projection data,
register respective reconstructed images of the plurality of projection data to the first projection data, and
perform a material decomposition using forward projections of the first projection data and the registered reconstructed images of the plurality of projection data.

11. The apparatus of claim 1, wherein the processing circuitry is further configured to
obtain a plurality of projection data representing radiation intensities incident on the plurality of detectors, the radiation intensities corresponding to a plurality of photon energies, and the plurality of projection data including the second projection data, but not including the first projection data,
generate respective motion images corresponding to each projection data of the plurality of projection data by
registering respective reconstructed images of each projection data of the plurality of projection data to the first projection data,
taking differences between respective registered reconstructed images of the plurality of projection data and a reconstructed image of the first projection data to generate a plurality of motion images,
forward projecting the plurality of motion images to generate a plurality of motion projection data, and
combining the plurality of motion projection data with the plurality of projection data to generate a corrected plurality of projection data including the updated second projection data, and
perform a material decomposition using the first projection data and the corrected plurality of projection data.

12. An apparatus, comprising:
an X-ray source configured to radiate X-rays;
a plurality of detector elements configured to
detect first projection data representing an X-ray intensity of first radiation incident at a plurality of detector elements during a first scan, the first radiation having a first X-ray energy, and
detect second projection data representing an X-ray intensity of second radiation incident at the plurality of detector elements during a second scan, the second radiation having a second X-ray energy; and
processing circuitry configured to
register a reconstructed image of the second projection data to a reconstructed image of the first projection data,
update the second projection data using the registered reconstructed image of the second projection data, and
perform material decomposition using the updated second projection data and an updated first projection data or the first projection data.

13. The apparatus of claim 12, wherein the processing circuitry is further configured to
forward project the registered reconstructed image of the second projection data to generate processed second projection data as the updated second projection data, forward project the reconstructed image of the first projection data to generate processed first projection data, and
perform material decomposition using the processed first projection data and the processed second projection data.

14. The apparatus of claim 12, wherein the processing circuitry is further configured to
generate a motion image by taking a difference between the reconstructed image of the second projection data without registration and the registered reconstructed image of the second projection data,
forward project the motion image to generate motion projection data,
combine the motion projection data with the second projection data to generate corrected second projection data as the updated second projection data, and
perform material decomposition using the first projection data and the corrected second projection data.

15. A method, comprising:
obtaining first projection data representing an intensity of first radiation incident at a plurality of detector elements, the first radiation having a first photon energy;
obtaining second projection data representing an intensity of second radiation incident at the plurality of detector elements, the second radiation having a second photon energy;
registering a reconstructed image of the second projection data to a reconstructed image of the first projection data;
updating the second projection data using the registered reconstructed image of the second projection data; and
performing material decomposition using the updated second projection data and an updated first projection data or the first projection data.

16. The method of claim 15, further comprising:
forward projecting the registered reconstructed image of the second projection data to generate processed second projection data as the updated second projection data;
forward projecting the reconstructed image of the first projection data to generate processed first projection data; and
performing material decomposition using the processed first projection data and the processed second projection data.

17. The method of claim 15, further comprising:
generating a motion image by taking a difference between the registered reconstructed image of the second projection data and the reconstructed image of the second projection data without registration;
forward projecting the motion image to generate motion projection data;
combining the motion projection data with the second projection data to generate corrected second projection data as the updated second projection data; and
performing material decomposition using the first projection data and the corrected second projection data.

18. A non-transitory computer-readable storage medium including executable instructions, wherein the instructions, when executed by circuitry, cause the circuitry to perform the method according to claim 15.

19. The non-transitory computer readable storage medium of claim 18, wherein the instructions further cause the circuitry to
forward project the registered reconstructed image of the second projection data to generate processed second projection data as the updated second projection data, forward project the reconstructed image of the first projection data to generate processed first projection data, and perform material decomposition using the processed first projection data and the processed second projection data.

20. The non-transitory computer readable storage medium of claim 18, wherein the instructions further cause the circuitry to generate a motion image by taking a difference between the reconstructed image of the second projection data without registration and the registered reconstructed image of the second projection data, forward project the motion image to generate motion projection data, combine the motion projection data with the second projection data to generate corrected second projection data as the updated second projection data, and perform material decomposition using the first projection data and the corrected second projection data.

* * * * *